United States Patent
Saint et al.

(10) Patent No.: US 10,864,327 B2
(45) Date of Patent: Dec. 15, 2020

(54) AUTOMATIC MEDICATION DELIVERY TRACKING

(71) Applicant: Companion Medical, Inc., San Diego, CA (US)

(72) Inventors: Sean Saint, San Diego, CA (US); Jack Pryor, Ladera Ranch, CA (US); Arnold Holmquist, Temecula, CA (US)

(73) Assignee: Companion Medical, Inc., San Diego, CA (US)

( * ) Notice: Subject to any disclaimer, the term of this patent is extended or adjusted under 35 U.S.C. 154(b) by 180 days.

(21) Appl. No.: 16/070,204

(22) PCT Filed: Jan. 27, 2017

(86) PCT No.: PCT/US2017/015452
§ 371 (c)(1),
(2) Date: Jul. 13, 2018

(87) PCT Pub. No.: WO2017/132577
PCT Pub. Date: Aug. 3, 2017

(65) Prior Publication Data
US 2019/0015596 A1   Jan. 17, 2019

Related U.S. Application Data

(60) Provisional application No. 62/289,082, filed on Jan. 29, 2016.

(51) Int. Cl.
*A61M 5/315*        (2006.01)
*G16H 20/17*        (2018.01)
(Continued)

(52) U.S. Cl.
CPC ...... *A61M 5/31546* (2013.01); *A61M 5/3202* (2013.01); *G16H 20/13* (2018.01);
(Continued)

(58) Field of Classification Search
CPC ........ G16H 20/17; G16H 40/63; G16H 50/20; G16H 20/13; A61M 5/31546;
(Continued)

(56) References Cited

U.S. PATENT DOCUMENTS

| 4,498,904 A | 2/1985 | Turner et al. |
| 4,515,584 A | 5/1985 | Abe et al. |

(Continued)

FOREIGN PATENT DOCUMENTS

| EP | 0298067 | 4/1989 |
| EP | 513128 | 11/1992 |

(Continued)

OTHER PUBLICATIONS

Cision PR News Wire, "CompaNion Medical Announces Insights by InPen, the Future of MDI Reports", Jun. 20, 2018.
(Continued)

*Primary Examiner* — Bhisma Mehta
*Assistant Examiner* — James D Ponton
(74) *Attorney, Agent, or Firm* — Carter, DeLuca & Farrell LLP

(57) ABSTRACT

Methods, systems, and devices are disclosed for tracking delivery of medication. In one aspect, a medication delivery tracking device can interface with and be physically placed on a medication delivery pen device. The medication delivery tracking device can detect an occurrence of a delivery of a medication by the medication delivery pen device. In some implementations, the medication delivery tracking device can detect a dose amount of the medication delivered by the medication delivery pen device.

18 Claims, 4 Drawing Sheets

(51) Int. Cl.
*G16H 40/63* (2018.01)
*G16H 50/20* (2018.01)
*G16H 20/13* (2018.01)
*A61M 5/32* (2006.01)

(52) U.S. Cl.
CPC .............. *G16H 20/17* (2018.01); *G16H 40/63* (2018.01); *G16H 50/20* (2018.01); *A61M 2205/18* (2013.01); *A61M 2205/332* (2013.01); *A61M 2205/3375* (2013.01); *A61M 2205/3389* (2013.01); *A61M 2205/3561* (2013.01); *A61M 2205/3584* (2013.01); *A61M 2205/50* (2013.01); *A61M 2205/505* (2013.01); *A61M 2205/581* (2013.01); *A61M 2205/582* (2013.01); *A61M 2205/583* (2013.01); *A61M 2209/06* (2013.01); *A61M 2230/201* (2013.01)

(58) Field of Classification Search
CPC . A61B 5/14532; A61B 5/4839; A61B 5/0002; A61B 5/0022
See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,133,329 B2 | 11/2006 | Skyggebjerg et al. |
| 7,397,730 B2 | 7/2008 | Skyggebjerg et al. |
| 7,591,801 B2 | 9/2009 | Brauker et al. |
| 7,905,833 B2 | 3/2011 | Brister et al. |
| 7,955,303 B2 | 6/2011 | Burren et al. |
| 7,976,492 B2 | 7/2011 | Brauker et al. |
| 8,052,655 B2 | 11/2011 | Moeller et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,743,662 B2 | 6/2014 | Sjolund et al. |
| 8,750,955 B2 | 6/2014 | Mensinger et al. |
| 8,808,228 B2 | 8/2014 | Brister et al. |
| 8,817,258 B2 | 8/2014 | Whalley et al. |
| 8,821,452 B2 | 9/2014 | Dasbach et al. |
| 8,882,722 B2 | 11/2014 | Bode et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| 9,089,650 B2 | 7/2015 | Nielsen et al. |
| 9,101,723 B2 | 8/2015 | Larsen |
| 9,108,006 B2 | 8/2015 | Jensen et al. |
| D738,385 S | 9/2015 | Lim et al. |
| 9,125,991 B2 | 9/2015 | Schabbach et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| 9,233,210 B2 | 1/2016 | Bock et al. |
| D749,103 S | 2/2016 | Song |
| 9,250,111 B2 | 2/2016 | Whalley et al. |
| 9,255,830 B2 | 2/2016 | Whalley et al. |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| 9,483,620 B2 | 11/2016 | Reimer |
| 9,526,838 B2 | 12/2016 | Baran et al. |
| D777,760 S | 1/2017 | Zhao et al. |
| 9,545,482 B2 | 1/2017 | Binier |
| D781,890 S | 3/2017 | Gathman et al. |
| 9,604,004 B2 | 3/2017 | Jakobsen |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| 9,619,625 B2 | 4/2017 | Bengtsson |
| 9,623,188 B2 | 4/2017 | Nielsen et al. |
| D786,273 S | 5/2017 | Herman et al. |
| 9,636,461 B2 | 5/2017 | Bengtsson et al. |
| 9,636,464 B1 | 5/2017 | Binier |
| 9,638,564 B2 | 5/2017 | Whalley et al. |
| 9,642,968 B2 | 5/2017 | Whalley et al. |
| 9,649,448 B2 | 5/2017 | Madsen |
| 9,651,482 B2 | 5/2017 | Blei et al. |
| 9,672,328 B2 | 6/2017 | Saint |
| 9,675,761 B2 | 6/2017 | Hoeholt et al. |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| 9,721,176 B2 | 8/2017 | Prager |
| 9,734,302 B2 | 8/2017 | Nielsen et al. |
| 9,737,665 B2 | 8/2017 | Neumann et al. |
| D797,760 S | 9/2017 | Tsujimura et al. |
| D798,312 S | 9/2017 | Tsujimura et al. |
| 9,750,882 B2 | 9/2017 | Blei et al. |
| 9,750,886 B2 | 9/2017 | Plambech et al. |
| 9,775,543 B2 | 10/2017 | Brister et al. |
| 9,782,543 B2 | 10/2017 | Groeschke et al. |
| 9,782,544 B2 | 10/2017 | Heumann et al. |
| 9,789,260 B1 | 10/2017 | Binier |
| 9,790,977 B2 | 10/2017 | Baran et al. |
| D802,760 S | 11/2017 | Neby |
| 9,833,576 B2 | 12/2017 | Windum et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| 10,016,565 B2 | 7/2018 | Nielsen et al. |
| 10,043,093 B2 | 8/2018 | Allerdings et al. |
| 10,071,205 B2 | 9/2018 | Blei et al. |
| D831,049 S | 10/2018 | Agarwal et al. |
| D831,684 S | 10/2018 | Ghosh |
| D832,292 S | 10/2018 | Hu et al. |
| 10,086,141 B2 | 10/2018 | Steel et al. |
| 10,105,094 B2 | 10/2018 | Baran et al. |
| 10,105,497 B2 | 10/2018 | Dreier et al. |
| D832,870 S | 11/2018 | Hu |
| D833,469 S | 11/2018 | Coleman et al. |
| D834,710 S | 11/2018 | Michael |
| 10,117,996 B2 | 11/2018 | Stefansen |

(56) References Cited

U.S. PATENT DOCUMENTS

| | | |
|---|---|---|
| 10,117,999 B2 | 11/2018 | Andersen |
| 10,133,948 B2 | 11/2018 | Hammen |
| D835,118 S | 12/2018 | Lee et al. |
| 10,155,090 B2 | 12/2018 | Larsen et al. |
| 10,159,797 B2 | 12/2018 | Andersen et al. |
| 10,159,798 B2 | 12/2018 | Blei et al. |
| D837,807 S | 1/2019 | Baber et al. |
| D838,734 S | 1/2019 | Kruse et al. |
| 10,166,338 B2 | 1/2019 | Nielsen et al. |
| 10,166,340 B2 | 1/2019 | Blei et al. |
| 10,169,539 B2 | 1/2019 | Reihman et al. |
| 10,179,207 B2 | 1/2019 | Haupt |
| 10,183,119 B2 | 1/2019 | Andersen et al. |
| 10,183,120 B2 | 1/2019 | Sihlanick et al. |
| 10,190,901 B2 | 1/2019 | Whalley et al. |
| 10,195,351 B2 | 2/2019 | Allerdings et al. |
| 10,195,352 B2 | 2/2019 | Baran et al. |
| 10,195,355 B2 | 2/2019 | Allerdings et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0228057 A1 | 9/2008 | Graskov et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0292634 A1* | 11/2010 | Kircher, Jr. ........ A61B 5/14532 604/66 |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0207080 A1 | 7/2014 | Allerdings |
| 2014/0257065 A1 | 9/2014 | Walsh |
| 2014/0276531 A1 | 9/2014 | Walsh |
| 2014/0288494 A1 | 9/2014 | Brister et al. |
| 2014/0324020 A1 | 10/2014 | Stefansen |
| 2014/0371682 A1 | 12/2014 | Bengtsson et al. |
| 2015/0073337 A1 | 3/2015 | Saint et al. |
| 2015/0202375 A1 | 7/2015 | Schabbach et al. |
| 2015/0202377 A1 | 7/2015 | Haupt |
| 2015/0306304 A1 | 10/2015 | Schabbach et al. |
| 2015/0351683 A1 | 12/2015 | Brauker et al. |
| 2015/0356273 A1 | 12/2015 | Cave |
| 2015/0359965 A1 | 12/2015 | O'Connor et al. |
| 2016/0012205 A1 | 1/2016 | Saint |
| 2016/0030673 A1 | 2/2016 | White et al. |
| 2016/0030679 A1 | 2/2016 | Nielsen et al. |
| 2016/0030680 A1 | 2/2016 | Veasey et al. |
| 2016/0030683 A1 | 2/2016 | Taylor |
| 2016/0038675 A1* | 2/2016 | Estes ...................... G06F 19/00 604/506 |
| 2016/0047685 A1 | 2/2016 | Blei et al. |
| 2016/0051760 A1 | 2/2016 | Krusell et al. |
| 2016/0065799 A1 | 3/2016 | Haupt et al. |
| 2016/0066843 A1 | 3/2016 | Mensinger et al. |
| 2016/0081632 A1 | 3/2016 | Kamath et al. |
| 2016/0082192 A1 | 3/2016 | Veasey et al. |
| 2016/0101232 A1 | 4/2016 | Kamath et al. |
| 2016/0101234 A1 | 4/2016 | Bock et al. |
| 2016/0106927 A1 | 4/2016 | Moeller et al. |
| 2016/0235925 A1 | 8/2016 | Kuhn et al. |
| 2016/0263327 A1 | 9/2016 | Radmer et al. |
| 2016/0287804 A1 | 10/2016 | Madsen et al. |
| 2016/0287807 A1 | 10/2016 | Madsen et al. |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0132392 A1 | 5/2017 | Gerken |
| 2017/0138769 A1 | 5/2017 | Jones et al. |
| 2017/0151390 A1 | 6/2017 | Muller-pathle |
| 2017/0182258 A1 | 6/2017 | Michael |
| 2017/0185283 A1 | 6/2017 | Bhavaraju et al. |
| 2017/0185284 A1* | 6/2017 | Bhavaraju ........... G06F 3/04883 |
| 2017/0189616 A1 | 7/2017 | Bengtsson et al. |
| 2017/0189625 A1 | 7/2017 | Cirillo et al. |
| 2017/0219486 A1 | 8/2017 | Blei et al. |
| 2017/0224922 A1 | 8/2017 | Lepple-wienhues |
| 2017/0224927 A1 | 8/2017 | Windum et al. |
| 2017/0232203 A1 | 8/2017 | Krusell |
| 2017/0235919 A1 | 8/2017 | Bauss et al. |
| 2017/0235920 A1 | 8/2017 | Bauss et al. |
| 2017/0266389 A1 | 9/2017 | Mcloughlin et al. |
| 2017/0270276 A1 | 9/2017 | Saint et al. |
| 2017/0270829 A1 | 9/2017 | Bauss |

(56) References Cited

U.S. PATENT DOCUMENTS

| | | |
|---|---|---|
| 2017/0286194 A1 | 10/2017 | Morris et al. |
| 2017/0286614 A1 | 10/2017 | Morris et al. |
| 2017/0304538 A1 | 10/2017 | Renstad et al. |
| 2017/0304541 A1 | 10/2017 | Bauss et al. |
| 2017/0304552 A1 | 10/2017 | Prager |
| 2017/0312446 A1 | 11/2017 | Kunz et al. |
| 2017/0316178 A1 | 11/2017 | Riedel et al. |
| 2017/0338864 A1 | 11/2017 | Rolsted et al. |
| 2017/0340808 A1 | 11/2017 | Andersen et al. |
| 2017/0340826 A1 | 11/2017 | Draper |
| 2017/0366617 A1 | 12/2017 | Mensinger et al. |
| 2017/0367627 A1 | 12/2017 | Brister et al. |
| 2017/0368263 A1 | 12/2017 | Ploch |
| 2017/0368265 A1 | 12/2017 | Groeschke et al. |
| 2018/0001027 A1 | 1/2018 | Klemm et al. |
| 2018/0008773 A1 | 1/2018 | Hautaviita et al. |
| 2018/0008778 A1 | 1/2018 | Erbstein |
| 2018/0008779 A1 | 1/2018 | Hautaviita et al. |
| 2018/0028759 A1 | 2/2018 | Riedel et al. |
| 2018/0028760 A1 | 2/2018 | Gugl et al. |
| 2018/0036484 A1 | 2/2018 | Andersen |
| 2018/0043104 A1 | 2/2018 | Mueller-Pathle |
| 2018/0050157 A1 | 2/2018 | Whalley et al. |
| 2018/0064879 A1 | 3/2018 | Säll et al. |
| 2018/0085532 A1 | 3/2018 | Desborough et al. |
| 2018/0099084 A1 | 4/2018 | Schabbach et al. |
| 2018/0154086 A1 | 6/2018 | Toporek et al. |
| 2018/0161505 A1 | 6/2018 | Prager |
| 2018/0185587 A1 | 7/2018 | Brauker et al. |
| 2018/0200451 A1 | 7/2018 | Shekalim |
| 2018/0221582 A1 | 8/2018 | Klemm et al. |
| 2018/0224315 A1 | 8/2018 | Schabbacha et al. |
| 2018/0228977 A1 | 8/2018 | Schabbach et al. |
| 2018/0236172 A1 | 8/2018 | Schabbach et al. |
| 2018/0236185 A1 | 8/2018 | Säll et al. |
| 2018/0243504 A1 | 8/2018 | Scott et al. |
| 2018/0268236 A1 | 9/2018 | Klemm |
| 2018/0272072 A1 | 9/2018 | Radmer et al. |
| 2018/0296767 A1 | 10/2018 | Säll |
| 2018/0303417 A1 | 10/2018 | Mensinger et al. |
| 2018/0304028 A1 | 10/2018 | Riedel |
| 2018/0326164 A1 | 11/2018 | Bauss et al. |
| 2018/0339113 A1 | 11/2018 | Wendland et al. |
| 2018/0341826 A1 | 11/2018 | Allerdings et al. |
| 2018/0353694 A1 | 12/2018 | Riedel et al. |
| 2018/0353698 A1 | 12/2018 | Saint et al. |
| 2018/0353699 A1 | 12/2018 | Helmer et al. |
| 2018/0353700 A1 | 12/2018 | SÄll et al. |
| 2018/0361067 A1 | 12/2018 | Säll et al. |
| 2018/0361076 A1 | 12/2018 | Klemm et al. |
| 2018/0361082 A1 | 12/2018 | Säll et al. |
| 2018/0369488 A1 | 12/2018 | Carlsson et al. |
| 2018/0369490 A1 | 12/2018 | Rehbein et al. |
| 2019/0001060 A1 | 1/2019 | Gylleby et al. |
| 2019/0001069 A1 | 1/2019 | Carlsson et al. |
| 2019/0009032 A1 | 1/2019 | Hautaviita et al. |
| 2019/0015020 A1 | 1/2019 | Brister et al. |
| 2019/0022320 A1 | 1/2019 | Carlsson et al. |
| 2019/0029590 A1 | 1/2019 | Baran et al. |
| 2019/0030250 A1 | 1/2019 | Steel et al. |
| 2019/0035500 A1 | 1/2019 | Saint et al. |
| 2019/0132801 A1 | 5/2019 | Kamath et al. |
| 2019/0173885 A1 | 6/2019 | Kamath et al. |
| 2019/0125224 A1 | 8/2019 | Kamath et al. |

FOREIGN PATENT DOCUMENTS

| | | |
|---|---|---|
| EP | 927057 | 7/1999 |
| EP | 2572740 | 3/2013 |
| WO | 9638190 | 12/1996 |
| WO | 2010052275 | 5/2010 |
| WO | 2011041007 | 4/2011 |
| WO | 2012046199 | 4/2012 |
| WO | 2013053695 | 4/2013 |
| WO | 2014029621 A1 | 2/2014 |
| WO | 2014128157 | 8/2014 |
| WO | 2015047870 | 4/2015 |
| WO | 2015169814 | 11/2015 |
| WO | 2015185686 | 12/2015 |
| WO | 2016071912 | 5/2016 |
| WO | 2017132577 | 3/2018 |

OTHER PUBLICATIONS

Copenheaver, B. R., Authorized Officer, ISA/US, International Search Report and Written Opinion, International Application No. PCT/US2014/056336, dated Dec. 31, 2014, 10 pages.

Young, Lee W., ISA/US, International Search Report, International Application No. PCT/US15/40069, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

International Search Report and Written Opinion for PCT Application No. PCT/US2018/036768; dated Aug. 31, 2018, 10 pages.

International Search Report and Written Opinion for PCT Application No. PCT/US2017/15452, dated May 23, 2017, 14 pages.

Extended European Search Report for European Patent Application No. 17745019.4, dated Aug. 6, 2019, 9 pages.

International Search Report and Written Opinion for PCT Application No. PCT/US2018/55646, dated Feb. 6, 2019, 15 pages.

* cited by examiner

AUTOMATIC MEDICATION DELIVERY TRACKING

CROSS-REFERENCE TO RELATED APPLICATIONS

This patent document is a 371 National Phase Application of PCT Application No. PCT/US2017/015452 entitled "AUTOMATIC MEDICATION DELIVERY SYSTEM" filed on Jan. 27, 2017, which claims priorities to and benefits of U.S. Provisional Patent Application No. 62/289,082 entitled "AUTOMATIC MEDICATION DELIVERY TRACKING" filed on Jan. 29, 2016. The entire contents of the aforementioned patent applications are incorporated by reference as part of the disclosure of this patent document.

TECHNICAL FIELD

This patent document relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering and tracking medicine to patients and providing health management capabilities for patients and caregivers.

In one aspect, a medication delivery tracking device for interfacing with and physical placement on a medication delivery pen device is disclosed. The medication delivery tracking device can detect an occurrence of a delivery of a medication by the medication delivery pen device.

In an example embodiment of a device for tracking medication delivery by a medication delivery pen, the device includes a body structured to interface with and reversibly attach to a portion of a medication delivery pen; a sensor to detect an occurrence of a delivery of a medication by the medication delivery pen; and a data processing unit configured to communicate with a companion computing device and transmit data associated with the detected occurrence of the delivery of the medication by the medication delivery pen to the companion computing device.

In an example embodiment of a computer-implemented method of applying an artificial pancreas algorithm in a diabetes management system including a glucose monitor device, an insulin delivery pen, and a smartphone including a software application including instructions executable by a processor of the smartphone to cause the smartphone to implement the method, the method includes receiving or determining a blood sugar level of a user; receiving or determining a dose amount of insulin delivered; based on the received or determined the blood sugar level and dose amount of insulin delivered, determining whether a predetermined amount of insulin is needed to lower the blood sugar level to a predetermined blood sugar level; and upon determination that the predetermined amount of insulin is needed, determining when to prompt the user to administer an additional dose of insulin comprising the predetermined amount of insulin.

In an example embodiment of a method of reporting of insulin delivery statistics, the method includes automatically scaling a medication delivery graph by setting a maximum dose value displayed on the graph based on a maximum dose entered into user settings.

In an example embodiment of a method of activating periodic dose delivery settings, the method includes receiving from a user a touch input indicating an activation of one or more of preexisting timed settings for delivering a dose of medication.

In an example embodiment of a method of activating a medication delivery system, the method includes detecting, at a companion device, a medication delivery device for pairing; pairing with the detected medication delivery device; and disabling a dose calculator on the companion device until the pairing is successful.

In an example embodiment of a mechanical sensor for tracking insulin delivery in a medication delivery device, the mechanical sensor includes a multichannel encoder to provide multiple normal states and multiple abnormal states, wherein a detection of one of the abnormal states indicates an error on the encoder.

DETAILED DESCRIPTION

Figure 1A:
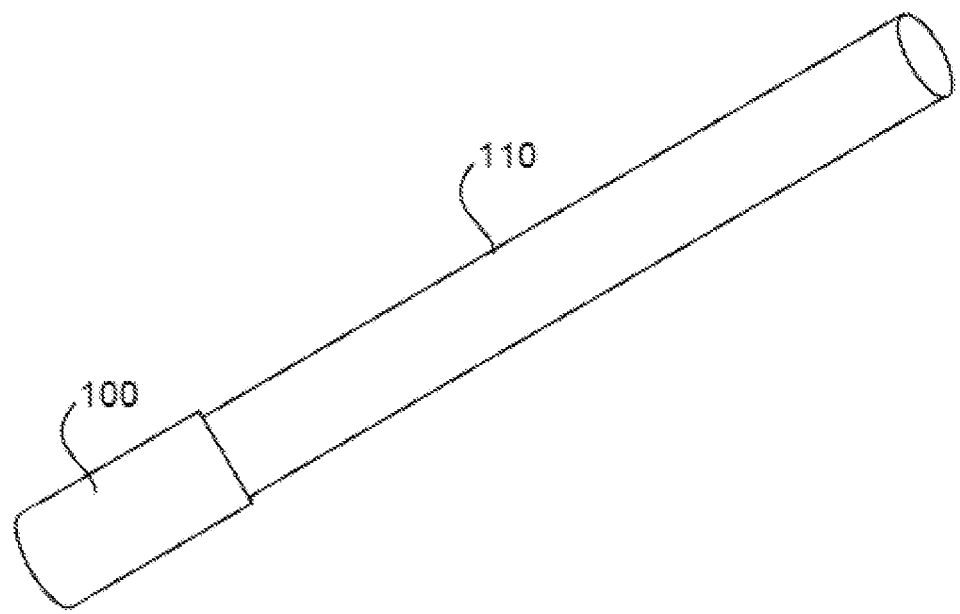
FIG. 1A shows an example embodiment of a smart cap implemented as a replacement cap device.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen, also referred to as a pen, is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been automated ways to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

Smart Cap for a Medication Pen

Various implementations and examples of the disclosed technology can be used to develop a smart cap for a medication pen. The smart cap according to the disclosed technology can be designed to be placed on or integrated with a conventional medication pen, such as an insulin pen or other type of medication pen, to facilitate tracking of the medicine delivered by that medication pen, e.g., such as tracking that a delivery event occurred, tracking the dose, tracking the time of delivery, etc. In some implementations, the smart cap can be designed for a rudimentary medication pen, such as a disposable insulin pen which typically does not have a mechanism to track delivery of the medication from the disposable pen. The smart cap can track various data (e.g., dose and temperature) related to the delivery of the medication by the medication pen and transmit the tracked data to a companion device, such as a smartphone, tablet, wearable communication device such as a smartwatch or the like, computer, web-server, etc.

Form Factor

The form factor for various embodiments of the smart cap can be designed to be a replacement for the existing ordinary cap used to cover the needle of the pen. FIG. 1A shows an example embodiment of a replacement smart cap 100. The replacement smart cap 100 fits on a medication pen 110 to replace an existing ordinary cap (not shown). In the replacement implementation, the smart cap 100 can perform certain operations when the smart cap is removed from the pen. For example, the smart cap 100 can be designed to transmit the tracked data when the smart cap 100 is removed from the pen.

Figure 1B:
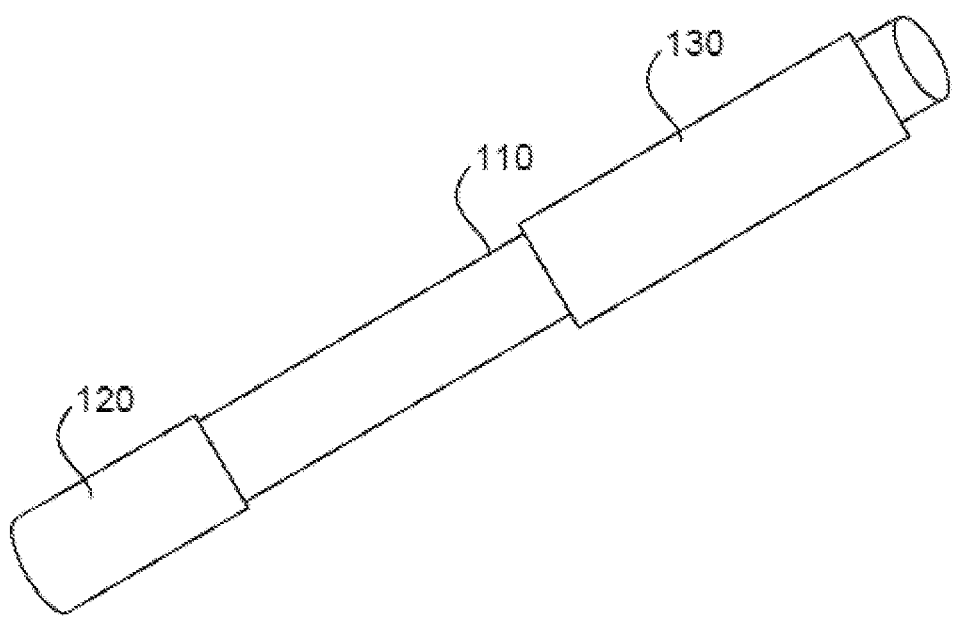
FIG. 1B shows an example embodiment of a smart cap implemented as an attachment device.

Alternatively, the smart cap can be designed as an attachment device (e.g., a sleeve) that attaches to or slips onto the medication pen. FIG. 1B shows an example embodiment of an attachment smart cap 130. The attachment smart cap 130 fits on a medication pen 110 as an attachment. In the attachment implementation, the medication pen 110 can maintain the existing ordinary cap 120. In the attachment implementation, the smart cap 130 does not need to be removed to perform certain operations, such as transmitting the tracked data. The smart cap 130 implemented as an attachment is removed from the medication pen 110 when switching to a new pen.

In some embodiments, the smart cap device may be a carrying case that holds the medication pen 110 (and optionally, additional pens or other devices). In implementations, the carrying case can detect removal of the pen 110, indicating that a dose is being taken. In some implementations, the carrying case may detect the amount of insulin used while the pen was removed, indicating the dose size. In some implementations, the carrying case may recharge a smart pen or smart device, such as smart cap 100 or 130, attached to a mechanical pen. In some implementations, the carrying case may download data temporarily stored in a smart pen or smart device and relay it to a companion device such as a smartphone.

Figure 1C:
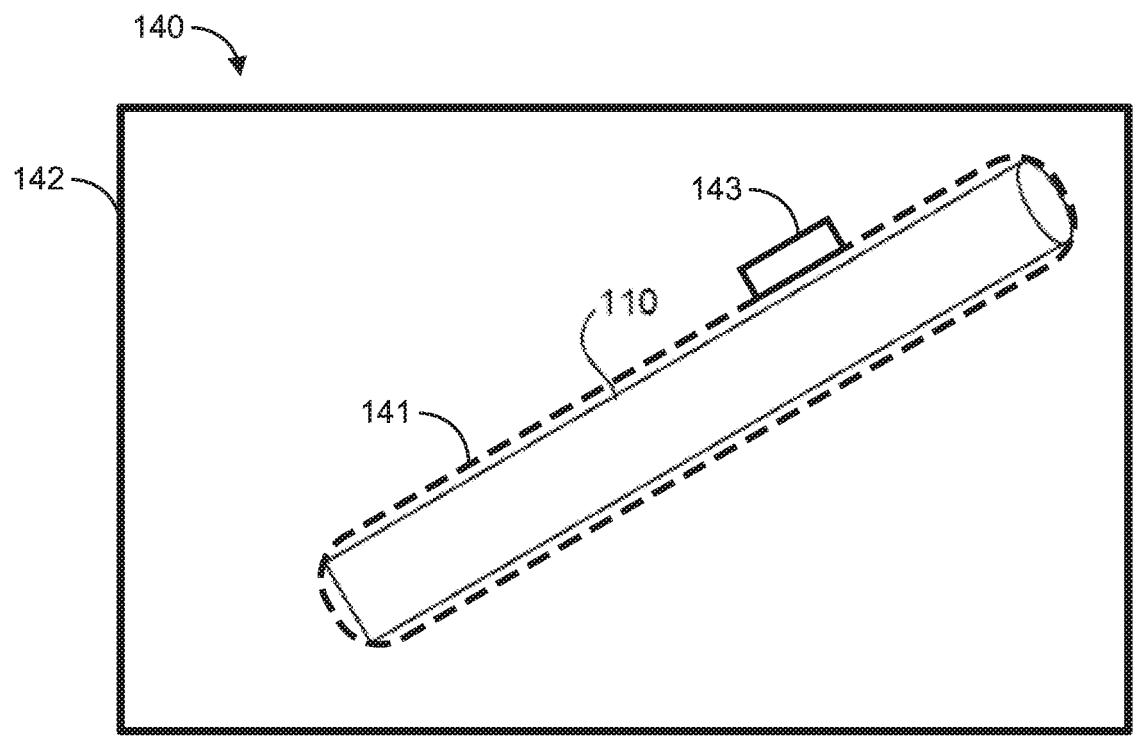
FIG. 1C shows an example embodiment of a smart cap implemented as a carrying case device.

FIG. 1C shows an example embodiment of a carrying case smart cap 140. The carrying case smart cap 140 includes a case body 142 having a cavity region 141 structured to allow the medication delivery pen 110 to be placed and held by the carrying case smart cap 140. The carrying case smart cap 140 includes a sensor 143 to detect the removal of the pen 110 from the cavity region 141. In some implementations, the sensor 143 detects an amount of insulin to be delivered when the pen is removed, indicating the dose size. For example, the cavity region 141 can allow an expanded cavity portion where the sensor 143 is positioned and aligned proximate to the dose dial-up component of the pen 110.

Figure 1D:
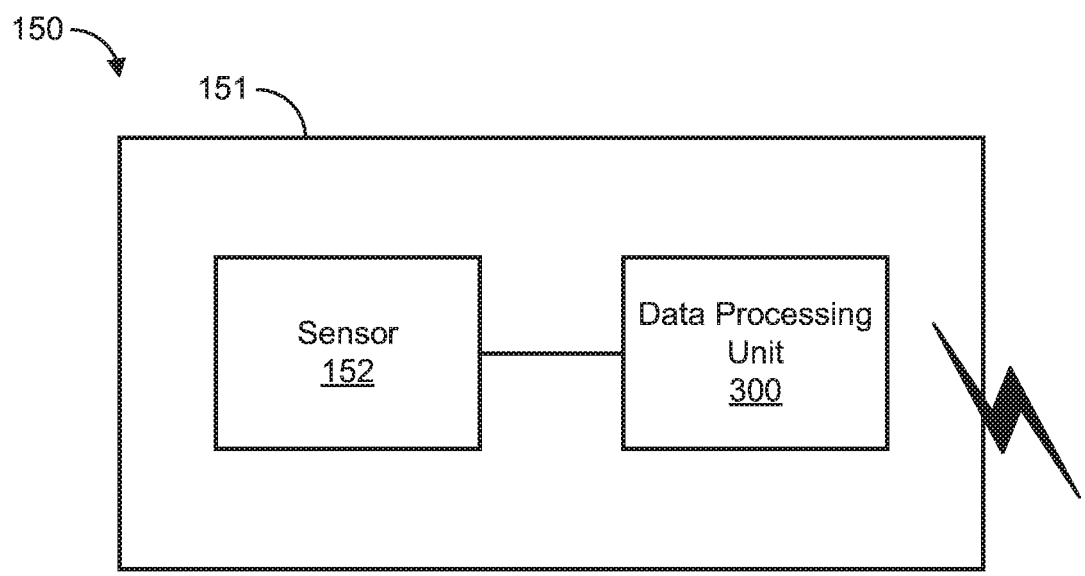
FIG. 1D shows a diagram of an example embodiment of a smart device in accordance with the disclosed technology.

FIG. 1D shows a diagram of an example embodiment of a smart device 150 for tracking medication delivery by a medication delivery pen. The smart device 150 can include various embodiments of the disclosed devices for tracking medication delivery, e.g., such as smart cap 100, 130 or 140. As depicted in FIG. 1D, the smart device 150 includes a body 151 structured to interface with and reversibly attach to a portion of a medication delivery pen (e.g., pen 110). The smart device 150 includes a sensor 152 to detect an occurrence of a delivery of a medication by the medication delivery pen 110. The sensor 152 can be coupled to the body 151 in a manner that integrates into the form factor of the smart device. In some implementations, the sensor 152 includes an audio transducer to detect a sound associated with a dose setting or dispensing of the medication performed by the pen 110, a rate sensor to detect a motion associated with a dose setting or dispensing of the medication performed by the pen 110, and/or a tactile sensor to detect a force or pressure associated with a dose setting or dispensing of the medication by the pen 110. The smart device 150 includes a data processing unit 300 configured to communicate with and transmit data and/or sensor signals to the companion device 200 associated with the detected occurrence of the delivery of the medication by the medication delivery pen 110. The data processing unit 300 is discussed later in FIG. 3. In various implementations of the smart device, the sensor can include a microphone, an accelerometer, a gyro sensor, and/or a strain gauge.

Tracking Dose Delivery

Various embodiments of the disclosed smart cap can automatically track medication delivery without requiring additional steps. For example, the disclosed smart cap can track that a dose (or a pre-set size of a dose) has been delivered regardless of whether or not the user has primed the pen. This way, the delivered dose can be accurately tracked without keeping track of any additional steps.

The disclosed technology provides for a number of different ways to track medication delivery using the smart cap. In some implementations, the smart cap can sense the audible or tactile feedback from the medication pen when the medication dose is "dialed up." For example, the mechanical dosing component of the medication pen requires a user to "dial up" a dose by turning a dial or wheel-like mechanical component. The act of dialing a dose can provide audible (e.g., "clicking sound"), rate (e.g., translational and/or angular acceleration or velocity) and tactile (e.g., resistance or vibrations felt when turning the dial or wheel) feedback. The smart cap can include an appropriate sound transducer or sensor, such as a microphone to listen for the clicks of the dial or wheel on the medication pen to determine the dose size. Similar techniques can be applied to "feel" the clicks using a tactile sensor, such as an accelerometer, pressure sensor and/or strain gauge. Also, techniques can be applied to detect the rate a mechanical component of the pen, such as the dial or wheel, moves.

Similarly, the smart cap can sense the audible or tactile feedback when the dose is dispensed from the medication pen. In some implementations, the smart cap may be positioned over the pen's dispensing button such that the smart cap itself is pressed to dispense the dose. For example, a sensor such as an electromechanical switch can detect when the dose is being dispensed so that it knows when to gather the audible or tactile input to detect dose size.

Insulin pens generally produce a clicking sound while dialing as an audio and a tactile feedback to the user, and some also produce a clicking sound during dosing. The clicking by the insulin delivery pens is related to dose size (e.g., a 3 unit dose may produce 3 clicks). For example, the clicks are generated mechanically by a detent or other snapping mechanism causing vibration which can be felt and heard.

In some examples, the medicament pen may produce different sounds when increasing or decreasing a pre-set dose, so that an audio sensor (e.g., sensor 152) can be used to differentiate between the different sounds, and thereby accurately deduce a final dialed dose amount.

In some implementations, the smart device 150 (e.g., smart cap 100, 130) can employ the sensor 152, e.g., an audio transducer (such as a microphone or piezoelectric element) and/or a vibration transducer (such as an accelerometer or electromagnetic pickup), to detect the clicks produced by the pen 110 when the user is setting a dose or delivery a dose. For example, the smart device 150 can be attached to the pen 110 such that the sensor 152 is operably coupled to the pen's mechanism that sets and/or delivers a dose of the medication such that the sensor is able to detect the sound and/or vibration from the 110 in a manner detectable at a much higher level than from other sources in the environment, e.g., in which the smart device 150 does not falsely interpret environmental noise as dosing information.

In some implementations, the smart device 150 can be coupled on or over the dispense button of the medication delivery pen 110, such that pressing on the smart device 150 will cause the pen 110 to dispense a dose, which would also allow an electrical pushbutton to be activated on the smart device 150 to detect when it is being depressed. In this way, for example, the smart device 150 detects clicks only when a dose is being dispensed, counting the clicks to indicate a dispensed amount, and avoid falsely counting sound or vibration from dialing or other handling of the device when not dispensing.

In some implementations, the smart device 150 could detect the clicks associated with the pen 110, in which detection uses a threshold detector with a timeout between detections. For example, when sound level exceeds a predetermined threshold (e.g., 60 dB), the smart device 150 counts that as a click and waits a brief delay period (e.g., 1 ms) for the sound to end before allowing detection of a subsequent click. Additionally or alternatively, for example, the smart device 150 can include a digital signal processor that applies pattern recognition techniques to detect the waveform of a click and differentiate it from environmental noise.

Prime Differentiation

The smart cap can be implemented for long-acting insulin delivery and tracking applications. Typically, for example, for long-acting insulin delivery, the same amount of insulin is delivered each time. Thus, the smart cap can be implemented to track the delivery of the long acting insulin without necessarily tracking the size of the dose. In some implementations, the smart cap includes a dosing dial that the user interfaces to enter the constant dose one time. Then, each time the smart cap is removed from the medication pen (or replaced), the smart cap can transmit the dialed-in constant dose to the companion device, such as a smartphone. When the user needs to adjust a dose, the physical dial can be adjusted. In some implementations, the smart cap is designed to simply transmit that a dose delivery of the constant dose has occurred (e.g., whenever the smart cap is removed or replaced from the medication pen). In this manner, the dose data recorded on the companion device is only that of the constant dose that the patient injected into his/her body using the pen.

In some implementations, the dose amount of the constant dose that is delivered when the smart cap transmits data that the dose has been delivered can be set on the companion device, such as on a smartphone using a smartphone application (also referred to as an "app"). In one example, the user sets a particular dose size and the application assumes that the user set dose was delivered each time a transmission is received from the smart cap. The user can override or adjust the tracked dose size through the smartphone application as needed.

Bonding/Pairing of the Pen and the Companion Device

In order to transmit the tracked dose data to a companion device, the smart cap can pair or bond with the companion device. A paired or bonded smart cap can be unpaired or unbonded through a specific unpairing or unbonding process.

Figure 2:
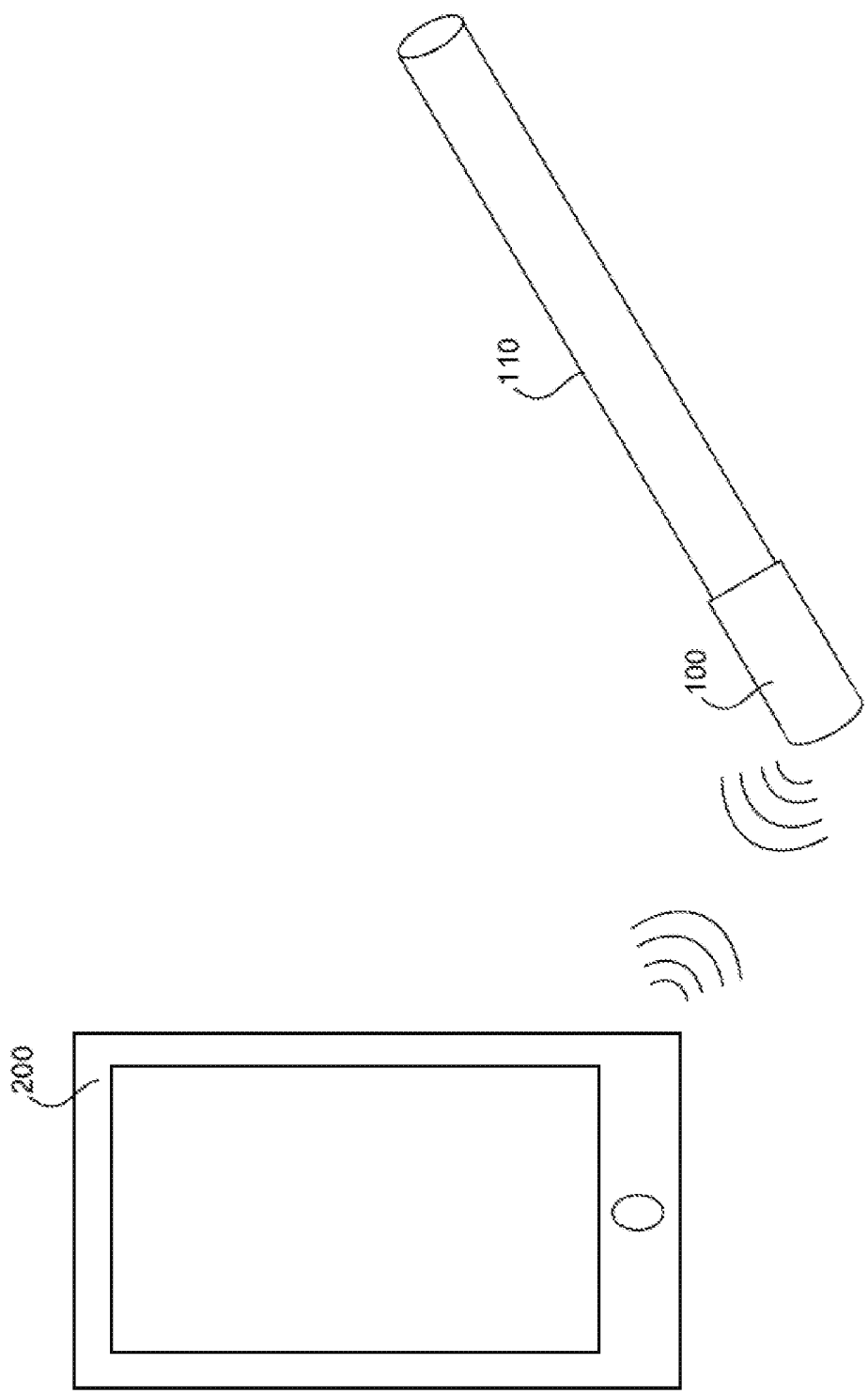
FIG. 2 shows an exemplary smart cap device pairing with a companion device.

FIG. 2 shows a smart cap bonding and unbonding with a companion device 200. The example of FIG. 2 illustrates the bonding or pairing of the smart cap 100 with the companion device 200, but it is understood that other embodiments of the smart cap can implement the bonding/unbonding or pairing/unpairing process, such as the smart cap 130. The smart cap 100 can be 'bonded' or 'paired' to the companion device 200 and 'unbonded' or 'unpaired' to the companion device 200 based on the following security communication methods. For example, the bonding of a particular smart cap device belonging to the user to a particular companion device of the user (e.g., the user's smartphone device, tablet, etc.) may need to be reset or cleared so that the particular smart cap may be bonded to a new companion device of the user or other (e.g., such as a new smartphone, tablet, etc. of the user). The bonding security feature can include a security code that the user enters on the companion device 200 via the user interface of the software application after the smart cap 100 is detected by the companion device 200 as a smart cap device to be bonded. The unbonding security feature can include a program stored in the memory of the smart cap 100 and/or in the cloud for providing to a new companion device, in which the program allows the unbonding to occur upon a particular pattern of detectable implementation events performed on the smart cap 100. For example, the program can unlock the smart cap-companion device bonding between the smart cap 100 and the initial companion device 200 (e.g., which may have been lost, damaged, or replaced by the user) when the user implements the pattern, e.g., and therefore allow the smart cap 100 to be bonded to another companion device of the user. For example, the program can include a pattern of events that correspond to a sequence. In one example, such unbonding sequence is effectuated by removing the smart cap 100 for a minimum of 5 seconds, followed by replacing the smart cap 100 for a minimum of 5 seconds, and repeating both steps again. Such a sequence can cause the smart cap 100 to be set back in a mode where it may be bonded or paired to a new companion device 200. Alternatively, or additionally, a button can be positioned on the smart cap 100 that resets the bonding of the smart cap 100. In one example, such a button is placed in a recessed position on the smart cap 100, which can be reset using, for example, an end of a paper clip.

In some implementations, the companion device can display the reset pattern to the user, e.g., to ensure that the user is aware of the pattern in the program capable of unbonding the pen-companion bonding relationship.

Reporting of Medication Delivery Statistics

Reporting of medication (e.g., insulin) delivery statistics can be confusing. For example, it can be difficult to determine the appropriate max-min values to scale the graphs of the medication delivery so that the graphs are visually informative to the user. In some implementations, the maximum value of the graph can be set as the maximum dose value or a value based on the maximum dose value that has been entered into the user settings. The maximum dose value A) is the largest dose of the medication expected to be delivered and B) should be set at a max threshold that is not much higher than a usual dose for safety mitigation. Using the maximum value based on the maximum dose allows the graphs to be scaled for each individual user and provides easily understandable visibility to the data in the graph. In this manner, for example, the max-min values scaled to the graph are automatically customized to the user, e.g., reducing complexities in the user's management of his/her health condition, such as diabetes. In some implementations, the maximum scale value does not need to be exactly the maximum dose setting but can be scaled based on the maximum dose, such as 1.1×, 2×, etc. of the maximum dose. Using the above described technique, a properly scaled graph is provided to each user, in which the limits on the graph stay constant over time, allowing the user to clearly view the relevant graphs on a consistent basis. The graph can be produced in a report, which can be provided to the user and/or a healthcare provider of the user, e.g., the user's physician(s), nurse(s), and/or caregivers such as family members, friends, and the like.

In some implementations, when reporting insulin usage, the report differentiates between insulin for glucose level correction and insulin for covering carbohydrate intake ('carb covering'), based on dose calculations. For example, reports can provide average daily amounts of correction and carb covering insulin. For example, reports can provide percentages of fast-acting insulin used for glucose level correction and for covering carbs, and possibly also long-acting insulin.

In some implementations, statistics are displayed graphically in an artistic image, animation, or video. In an example, the statistics are graphically displayed as a new animated flower blooms every time the dose calculator is used, so that over time many flowers are displayed, indicating that the dose calculator is being utilized frequently. This informs a physician or caregiver at a glance, and helps reinforce good behavior to the user. For example, graphical representation may be a separate report that may be viewed or transmitted. For example, graphical representation may be persistently visible on the companion device or the main app (e.g., as a background image on the user interface of the app) to give an intuitive overview of user compliance or success.

Customized User Profile for Administration of Medication

In some implementations, the user application on the companion device can include user customizable features. For example, the user can enter his/her medication delivery parameters in a variety of periodic delivery settings. Any number of delivery settings can be available on the application and the user can simply activate any number of the periodic delivery settings by simply touching a user selectable button, for example. Activated periodic delivery setting(s) can be programmed with specifics including the maximum dose amount, target blood sugar level, etc. In some implementations, for example, four delivery settings can pre-exist on the application representing medication delivery after breakfast, after lunch, after a snack, and after dinner. The exact time of day for each delivery setting can be determined by the user. When active (e.g., by user touch selection), the active delivery setting can provide an alarm, such as a sound, a light, a text message, etc., through the companion device, the smart cap, a smart pen, or a combination of the devices. The alarm can remind the user to administer the medication delivery as indicated on the active delivery settings. In some implementations, only one time setting is provided, whereby a single set of delivery settings are constantly active, e.g., for any time of day or type of meal. In still other implementations, the user can have a choice among two or more different time settings, whereby the delivery settings automatically change at preset times throughout the day. For example, the application makes available both the one and the four time settings such that either the one or the four time settings can be selected. In some implementations, the user can create additional settings or remove existing settings to simplify the user interface on the application. In some implementations, the user application on the companion device can include missed meal alarms (which are different from the previously described alarms associated with periodic delivery timed settings). In particular, missed meal alarms can be set for any meal separate from the timed settings. For example, the user may want the same carb factor all day long but be reminded to take the noontime dose. Or the user may want different timed settings all day and be reminded of only one dose or none at all.

Mechanical Sensor for Detecting Water Ingress

Tracking medication delivery through a medication pen or a smart cap can be performed using an appropriate sensor. In some aspects of the present technology, a mechanical encoder can be used to perform the medication delivery tracking. For example, a multichannel mechanical encoder can be used to detect impossible states that indicate a problematic issue, such as water ingress that causes short-circuiting of the system. In a multichannel encoder, a certain pattern of the encoder states are expected. For example, in a 2 channel (quadrature) encoder, there are 4 possible states, 1, 2, 3 and 4. However, in a 3 or 4 channel encoder, there can be positions or states which are not normally possible. Detection of the not normally possible states can indicate that encoder lines are shorted due to water ingress into the encoder, for example. When water ingress is detected, the medication pen or the smart cap can be disabled so as to prevent administration of the medication delivery for safety mitigation.

Application of Artificial Pancreas Algorithms to Pen System

In another aspect, artificial pancreas algorithms can be applied to a pen system. Artificial pancreas algorithms are used to track the blood sugar level of a person and the insulin dose delivered to determine when a person needs additional administration of insulin dose. When automatically delivered through a pump system, for example, it can result in what appears to be slightly higher basal rate because the artificial pancreas algorithms determine periodically (e.g., every 5 minutes or so) that the person needs slightly more insulin and cause the pump system to deliver a dose automatically. Such constant reminder of insulin delivery does not work with a pen system because the user would not want to be alerted to take insulin every 5 minutes (especially since the delivery is not automatic and must be manually dosed). In addition, the incremental amount of insulin that may need to be dosed each 5 minutes (or so) may be smaller than the smallest dose a pen can deliver.

The disclosed technology can be used to implement a minimum correction dose delivery feature. Using this feature, the system does not prompt a user to deliver a dose of insulin until the system determines that the person needs at least a predetermined amount of insulin (perhaps 1, 2 or 5 units) or that the user needs the required amount of insulin to lower his/her blood sugar by a predetermined amount (perhaps 20, 50 or 100 mg/dL) based on current or forecasted blood sugar level. The predetermined amount of insulin or the predetermined amount of blood sugar level can be determined from the user's correction factor which governs how much insulin is needed to lower the user's blood sugar level typically in units of mg/dL/Unit. For example, if the user had a correction factor of 50/1 mg/dl/U and a system required a minimum blood sugar change of 100 mg/dl, then the system will not alert the user until the system has determined that the user needs a minimum of 100/50=2 units. This allows artificial pancreas style algorithms to be applied to pen systems essentially unchanged. When additional insulin delivery is needed based on the tracking of the blood sugar level and the insulin delivery tracking, an alarm can be sent through the pen system to alert the user that the user should administer another dose of insulin, including the dose amount. In one implementation the following relationship is used to determine an amount of insulin needed:

Insulin needed=current blood sugar/correction factor−insulin on board.

In some embodiments, a method of applying an artificial pancreas algorithm to implement a minimum correction dose delivery using an insulin pen system includes tracking a blood sugar level (e.g., glucose level) of a user and tracking at least one dose amount of insulin delivered to the user. The method includes, based on the tracked blood sugar level and dose amount of insulin delivered, determining when to prompt the user to administer an additional dose of insulin, which is based on a determination that a predetermined amount of insulin is needed to lower the blood sugar level to a predetermined blood sugar level. For example, the predetermined amount of insulin can include 1, 2, or 5 units of insulin. For example, the user can be prompted to administer the additional dose of insulin by the system (e.g., app on the companion device and/or smart device) presenting an alarm to the user upon a determination that an amount of the additional dose of insulin that needs to be administered exceeds one or more predetermined threshold values. Or, for example, the user can be prompted to administer the additional dose of insulin by the system (e.g., app on the companion device and/or smart device) presenting an alarm to the user upon a determination that a required change in the user's blood sugar level to return to a predetermined target level (or target level range) is greater than or equal to a particular value, e.g., such as 20, 50 or 100 mg/dL, over the predetermined target blood sugar level or range. Implementations of the method are operable on the companion device via the application associated with the pen (e.g., pen 110) and/or smart device (e.g., smart cap 100, 130).

In some implementations, the method can be applied for minimizing correction doses using the insulin pen system, in which the method includes determining when to prompt the user to intake (e.g., eat) an amount of carbohydrates (e.g., to raise blood sugar levels to a predetermined blood sugar level).

In some embodiments, the method of applying an artificial pancreas algorithm includes a process to optimize treatment recommendations and/or conditions to minimize the number of injections per day. The process can include receiving or determining a preferred number of doses for injection per day, and/or preferred maximum number of doses for injection per day. For example, the preferred number of doses per day and the preferred maximum number of doses per day can be predetermined or user-selectable via the application on the companion device. The process can include an override of the preferred maximum number of doses, e.g., to be exceeded in severe or emergency cases. Similarly, the process to optimize treatment recommendations and/or conditions can include receiving or determining predetermined or user-selectable preferred minimum time delay between doses. In some implementations of the process to optimize treatment recommendations and/or conditions, the user may select a qualitative attribute, e.g., such as "aggressive" versus "relaxed", which can cause the system to adjust recommendation thresholds and therefore affect (e.g., minimize) how often a dose is suggested. In some implementations of the process to optimize treatment recommendations and/or conditions, the user may select a desired A1c or average glucose value (or a relative change value from the user's current levels of A1c or average glucose) that the user desires to achieve. In such implementations, the algorithm is adjusted to affect how 'strictly' the algorithm manages glucose and how often doses are suggested to the user, e.g., the prompting of the user to administer the additional doses. In some implementations, The process to optimize treatment recommendations and/or conditions can include receiving or determining a minimum time between doses that is based on a last dose size, e.g., where the prompting of the user to administer an additional dose is applied with respect to the minimum time and is thereby delayed longer after larger doses. The process to optimize treatment recommendations and/or conditions can include receiving or determining a minimum time between doses that is based on IOB, e.g., where the prompting of the user to administer the additional dose is delayed to wait longer when more insulin is active (on board) in the user's body.

In some embodiments, the method of applying an artificial pancreas algorithm includes a process to optimize treatment recommendations and/or conditions for best A1c levels with the fewest doses per day. The process can include delaying a correction recommendation if a scheduled dose is determined to occur soon, such as for lunchtime or bedtime. For example, the process to delay a correction dose can include, at least temporarily, increasing a triggering threshold for a correction dose recommendation. In some implementations, the app is configured to provide a user interface allowing the user to "snooze" a dose recommendation, e.g., such as when the user knows he/she will be eating soon and will need another dose anyway, so that doses may be combined into one. Similarly, for example, the smart device (e.g., smart cap 100, 130) can be configured to provide the dose recommendation alerts, e.g., via an visual display, haptic mechanism and/or audio display (e.g., speaker), and to provide an interface that allows the user to "snooze" the dose recommendation.

Similarly, the process to optimize treatment recommendations and/or conditions for best A1c levels can include, at least temporarily, decreasing a triggering threshold for a correction dose recommendation if no other scheduled doses are determined to occur soon. For example, implementation of the process can manage glucose level corrections in consideration of longer time periods, significantly reducing the area under the glucose curve even though the change in glucose may be small, which is contemplated to result in improved A1c levels. In an example, the process to temporarily decrease a trigger threshold to prompt the user to make a slight correction can be implemented one or more hours before bedtime. The process to optimize treatment recommendations and/or conditions for best A1c levels can include delaying a dose and/or increasing a triggering threshold for a dose recommendation when glucose is rising quickly so that a larger dose may be safely recommended, rather than an immediate small dose that may need to immediately be followed by another small dose.

In some implementations, the app is configured to provide a user interface allowing the user to set preferred "Do Not Disturb" times, such that alerts to recommend a dose are not executed. For example, the app can be configured to increase the recommendation threshold when the companion device (e.g., smartphone) is put in Do Not Disturb mode and concurrently monitor the glucose levels, so that a recommendation will only be made in severe or emergency cases with respect to a user's glucose levels. Similarly, the app can be configured to reduce the recommendation threshold prior to a Do Not Disturb time (e.g., a scheduled or pattern-based Do Not Disturb mode setting) so that a smaller correction may be suggested to minimize the chance of disruption. For example, the smaller correction dose may be based at least in part on a current or forecasted glucose level. The app can be configured to warn the user if a disruption (e.g., a dose or carb recommendation) is likely during an upcoming Do Not Disturb period based on a forecasted glucose level. For example, times may be pre-set, such as for sleep time; times may be set in real-time, such as tapping a button when arriving at a social event; and times may be related to events on the user's digital calendar, such as scheduled meetings.

Safety Mitigation

In another aspect, a medication delivery pen system can be implemented to disable the dose calculator until the pen system is coupled with a companion device. Because the medication pen device is dispensed to a user only under a doctor's prescription, when the medication pen pairs with a companion device, the dose calculator can change from disabled to activated to allow the user to start dose calculation and delivery.

Figure 3:
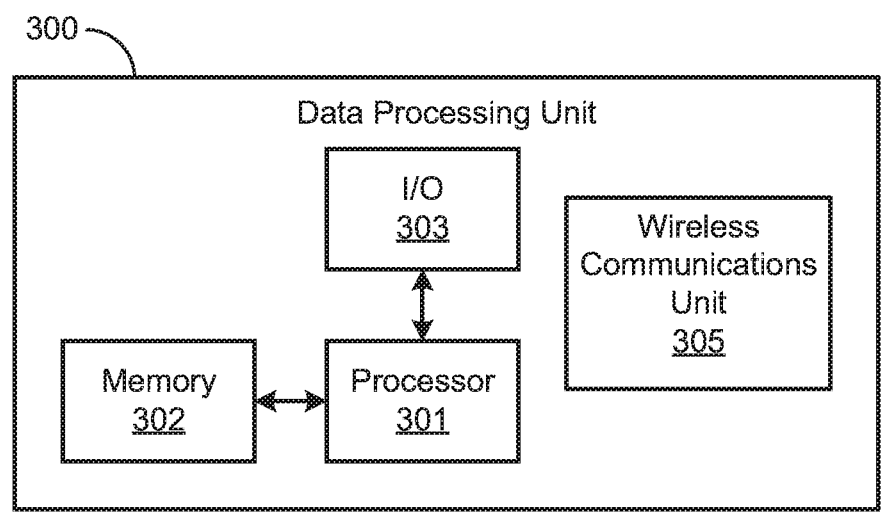
FIG. 3 shows a block diagram of an example embodiment of a data processing unit of the smart device.

FIG. 3 shows a block diagram of an example embodiment of a data processing unit 300 of a smart device in accordance with the disclosed technology, e.g., such as the smart cap 100 and the smart cap 130. The data processing unit 300 can include a processor 301 to process data, and a memory 302 in communication with the processor 301 to store and/or buffer data. For example, the processor 301 can include a central processing unit (CPU) or a microcontroller unit (MCU). For example, the memory 302 can include and store processor-executable code, which when executed by the processor, configures the data processing unit 300 to perform various operations, e.g., such as receiving information, commands, and/or data, processing information and data, and transmitting or providing information/data to another device. To support various functions of the data processing unit 300, the memory 302 can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory 302. In some implementations, the data processing unit 300 includes an input/output unit (I/O) 303 to interface the processor 301 and/or memory 302 to other modules, units or devices of the smart device, and/or external devices. The data processing unit 300 includes a wireless communications unit 305, e.g., such as a transmitter (Tx) or a transmitter/receiver (Tx/Rx) unit. In some implementations, the I/O 303 can interface the processor 301 and memory 302 with the wireless communications unit 305 to utilize various types of wireless interfaces compatible with typical data communication standards, for example, which can be used in communications of the data processing unit 300 with other devices such as the companion device 200, e.g., including, but not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. In some implementations, the data processing unit 300 can interface with other devices using a wired connection via the I/O of the data processing unit 300. The data processing unit 300 can also interface with other external interfaces, sources of data storage, and/or visual or audio display devices, etc. to retrieve and transfer data and information that can be processed by the processor 301, stored in the memory 302, or exhibited on an output unit of the companion device 200 or an external device. In some implementations, the data processing unit 300 can transmit raw or at least partially processed data or communication signals from the sensor of the smart device to the companion device 200. In some implementations, the data processing unit 300 can transmit raw or at least partially processed data to a computer system or communication network accessible via the Internet (referred to as 'the cloud') that includes one or more remote computational processing devices (e.g., servers in the cloud).

EXAMPLES

In an example embodiment of a device for tracking medication delivery by a medication delivery pen (example 1), the device includes a body structured to interface with and reversibly attach to a portion of a medication delivery pen; a sensor to detect an occurrence of a delivery of a medication by the medication delivery pen; and a data processing unit configured to communicate with a companion computing device and transmit data associated with the detected occurrence of the delivery of the medication by the medication delivery pen to the companion computing device.

Example 2 includes the device of example 1, in which the sensor includes one or more of an audio transducer, a rate sensor, or a tactile sensor.

Example 3 includes the device of example 2, in which the audio transducer includes a microphone.

Example 4 includes the device of example 2, in which the rate sensor includes one or both of an accelerometer or a gyro sensor.

Example 5 includes the device of example 2, in which the tactile sensor includes a strain gauge.

Example 6 includes the device of example 2, in which the device is configured to detect an audible feedback, a motion feedback, or a tactile feedback when a dose of the medication is set on the medication delivery pen.

Example 7 includes the device of example 6, in which the audible feedback includes a sound associated with setting of the dose on the medication delivery pen.

Example 8 includes the device of example 1, in which the device is configured to detect each instance of medication delivery by sensing removal or replacement of the device from the portion of the medication delivery pen to which the device is reversibly attached.

Example 9 includes the device of example 1, in which the device is configured to securely data pair with the companion computing device and transmit data associated with the detected occurrence of the delivery of the medication by the medication delivery pen to the paired companion computing device.

Example 10 includes the device of example 1, in which the device is a cap device shaped to fit on the medication delivery pen and replace an existing cap.

Example 11 includes the device of example 10, in which the cap device is configured to transmit data associated with the detected occurrence of the delivery of the medication by the medication delivery pen to the paired companion computing device when the cap device removed from the medication delivery pen.

Example 12 includes the device of example 1, in which the device is an attachment device shaped to fit on the medication delivery pen such that the attachment device does not replace an existing cap of the medication delivery pen.

Example 13 includes the device of example 12, in which the sensor of the attachment device is operable to when the existing cap is removed from the medication delivery pen.

Example 14 includes the device of example 1, in which the device is a carrying case configured to contain and store the medication delivery pen, and in which the sensor is operable to detect removal of the medication delivery pen.

Example 15 includes the device of example 1, in which the device is configured to track delivery of long acting insulin.

In an example embodiment of a computer-implemented method of applying an artificial pancreas algorithm in a diabetes management system including a glucose monitor device, an insulin delivery pen, and a smartphone including a software application including instructions executable by a processor of the smartphone to cause the smartphone to implement the method (example 16), the method includes receiving or determining a blood sugar level of a user; receiving or determining a dose amount of insulin delivered; based on the received or determined the blood sugar level and dose amount of insulin delivered, determining whether a predetermined amount of insulin is needed to lower the blood sugar level to a predetermined blood sugar level; and upon determination that the predetermined amount of insulin is needed, determining when to prompt the user to administer an additional dose of insulin comprising the predetermined amount of insulin.

Example 17 includes the method of example 16, in which the predetermined amount of insulin includes 1, 2, or 5 units of insulin.

Example 18 includes the method of example 16, in which the determining when to prompt the user to administer the additional dose of insulin includes presenting an alarm to the user upon a determination that an amount of additional dose of insulin that needs to be administered exceeds one or more predetermined threshold values.

Example 19 includes the method of example 16, in which the determining when to prompt the user to administer the additional dose of insulin includes presenting an alarm to the user upon a determination that a projected change in the blood sugar level caused by administration of the predetermined amount of insulin is greater than or equal to a particular value over the predetermined blood sugar level.

Example 20 includes the method of example 19, in which the particular value is in a range of 20 to 100 mg/dL over the predetermined blood sugar level.

Example 21 includes the method of example 16, in which the determining whether the predetermined amount of insulin is needed includes calculating an amount of insulin needed by: insulin needed=(current blood sugar/correction factor)−insulin on board.

In an example embodiment of a method of reporting of insulin delivery statistics (example 22), the method includes automatically scaling a medication delivery graph by setting a maximum dose value displayed on the graph based on a maximum dose entered into user settings.

Example 23 includes the method of example 22, in which the maximum dose value displayed is a multiple of the maximum dose entered into the use settings.

In an example embodiment of a method of activating periodic dose delivery settings (example 24), the method includes receiving from a user a touch input indicating an activation of one or more of preexisting timed settings for delivering a dose of medication.

Example 25 includes the method of example 24, in which the preexisting timed settings include either single timed setting or four timed settings. For example, the four timed settings are associated with a breakfast meal, a lunch meal, a dinner meal, and a snack.

In an example embodiment of a method of activating a medication delivery system (example 26), the method includes detecting, at a companion device, a medication delivery device for pairing; pairing with the detected medication delivery device; and disabling a dose calculator on the companion device until the pairing is successful.

In an example embodiment of a mechanical sensor for tracking insulin delivery in a medication delivery device (example 27), the mechanical sensor includes a multichannel encoder to provide multiple normal states and multiple abnormal states, wherein a detection of one of the abnormal states indicates an error on the encoder.

Example 28 includes the mechanical sensor of example 27, in which the multichannel encoder includes three or more channels.

Example 29 includes the mechanical sensor of example 27, in which the detection of one of the abnormal states indicates the error including water ingress into the encoder.

In an example embodiment of a method of applying an artificial pancreas algorithm in a diabetes management system using a smart device for tracking medication delivery by an insulin delivery pen as in example 1, where the diabetes management system includes a glucose monitor device and the insulin delivery pen (example 30), the method implemented by the smart device for tracking medication delivery includes: receiving or determining, at the data processing unit, a blood sugar level of a user; receiving or determining, at the data processing unit, a dose amount of insulin delivered; based on the received or determined the blood sugar level and dose amount of insulin delivered, determining at the data processing unit whether a predetermined amount of insulin is needed to lower the blood sugar level to a predetermined blood sugar level; and upon determination that the predetermined amount of insulin is needed, determining at the data processing unit when to prompt the user to administer an additional dose of insulin comprising the predetermined amount of insulin.

Example 31 includes the method of example 30, in which the determining the dose amount of insulin delivered is based at least in part on data received from the sensor detecting the delivery of the medication by the insulin delivery pen.

Example 32 includes the method of example 30, in which the predetermined amount of insulin includes 1, 2, or 5 units of insulin.

Example 33 includes the method of example 30, in which determining when to prompt the user to administer the additional dose of insulin includes presenting an alarm to the user upon a determination that an amount of additional dose of insulin that needs to be administered exceeds one or more predetermined threshold values.

Example 34 includes the method of example 33, in which the alarm is presented by the smart device via one or more of an audio display, a visual display or a haptic display of the smart device.

Example 35 includes the method of example 33, in which the diabetes management system further includes a software application operable on a mobile computing device such as a smartphone, tablet, or wearable device, the software application including instructions stored in a memory of and executable by a processor of the mobile computing device, and in which the determining when to prompt the user to administer the additional dose of insulin is determined by the software application and the alarm is presented by the mobile computing device.

Example 36 includes the method of example 30, in which determining when to prompt the user to administer the additional dose of insulin includes presenting an alarm to the user upon a determination that a projected change in the blood sugar level caused by administration of the predetermined amount of insulin is greater than or equal to a particular value over the predetermined blood sugar level.

Example 37 includes the method of example 36, in which the particular value is in a range of 20 to 100 mg/dL over the predetermined blood sugar level.

Example 38 includes the method of example 36, in which the alarm is presented by the smart device via one or more of an audio display, a visual display or a haptic display of the smart device.

Example 39 includes the method of example 36, in which the diabetes management system further includes a software application operable on a mobile computing device such as a smartphone, tablet, or wearable device, the software application including instructions stored in a memory of and executable by a processor of the mobile computing device, and in which the determining when to prompt the user to administer the additional dose of insulin is determined by the software application and the alarm is presented by the mobile computing device.

Example 40 includes the method of example 30, in which the determining whether the predetermined amount of insulin is needed includes calculating an amount of insulin needed by: insulin needed=(current blood sugar/correction factor)−insulin on board.

In some aspects, a medication delivery tracking device for interfacing with and physical placement on a medication delivery pen device is disclosed. The medication delivery tracking device can detect an occurrence of a delivery of a medication by the medication delivery pen device. The medication delivery tracking device can be implemented in various ways to provide one or more of the following features. For example, the medication delivery tracking device can detect each instance of the medication delivery by sensing removal or replacement of the medication delivery tracking device from or on pen device. The medication delivery tracking device can pair with a companion device and transmit data associated with the detected occurrence of the delivery of the medication by the medication delivery pen device to the paired companion device. The medication delivery tracking device can be a cap device shaped to fit on the medication delivery pen device and replace an existing cap. The cap device can transmit the data when removed from or replaced on the medication delivery pen device. The medication delivery tracking device can be an attachment device shaped to fit on the medication delivery pen device and not replace an existing cap device. The attachment device can transmit the data when removed from the medication delivery pen device. The medication delivery tracking device can detect an audible or tactile feedback when a dose is set on the medication delivery pen device. The audible feedback can include sound associated with setting of the dose on the medication delivery pen device. The medication delivery tracking device can track delivery of long acting insulin.

In some aspects, a method of reporting of insulin delivery statistics includes automatically scaling a medication delivery graph by setting a maximum dose value displayed on the graph based on a maximum dose entered into user settings. In one implementation, the preexisting timed settings include either a single timed setting or four timed settings. The method can be implemented in various ways to include one or more of the following features. The maximum dose value displayed can include a multiple of the maximum dose entered into the use settings.

In some aspects, a method of activating periodic dose delivery settings includes receiving from a user, a touch input indicating an activation of one or more of preexisting timed settings for delivering a dose of medication.

In some aspects, a mechanical sensor for tracking insulin delivery in a medication delivery device includes a multi-channel encoder to provide multiple normal states and multiple abnormal states. Detection of one of the abnormal states indicates an error on the encoder. The mechanical sensor can be implemented in various ways to include one or more of the following features. For example, the multi-channel encoder can include 3 or more channels. The detection of one of the abnormal states can indicate the error including water ingress into the encoder.

In some aspects, a method of applying an artificial pancreas algorithm in a pen system includes tracking a blood sugar level of a user; tracking a dose amount of insulin delivered; and based on the tracking of the blood sugar level and the dose amount of insulin delivered, determining when to prompt the user to administer an additional dose of insulin. The determining is based on a determination that a predetermined amount of insulin is needed to lower the blood sugar level to a predetermined blood sugar level. The method can be implemented in various ways to include one or more of the following features. For example, the predetermined amount of insulin can include 1, 2, or 5 units of insulin. In some implementations, determining when to prompt the user to administer the additional dose of insulin includes presenting an alarm to the user upon a determination that an amount of additional dose of insulin that needs to be administered exceeds one or more predetermined threshold values. In some implementations, wherein determining when to prompt the user to administer the additional dose of insulin includes presenting an alarm to the user upon a determination that a projected change in the blood sugar level upon administration of the predetermined amount of insulin is greater than or equal to a particular value over the predetermined blood sugar level. The particular value can be one of 20, 50 or 100 mg/dL.

In some aspects, a method of activating a medication delivery system includes detecting, at a companion device, a medication delivery device for pairing; pairing with the detected medication delivery device; and disabling a dose calculator on the companion device until the pairing is successful.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A computer-implemented method of applying an algorithm in a diabetes management system including a glucose monitor device, an insulin delivery pen, and a mobile communication device including a software application including instructions executable by a processor of the mobile communication device to cause the mobile communication device to implement the method, the method comprising:

receiving or determining a blood sugar level of a user;

receiving or determining a dose amount of insulin delivered;

based on the received or determined blood sugar level and the received or determined dose amount of insulin delivered, determining whether a predetermined amount of insulin is needed to lower the blood sugar level to a predetermined blood sugar level; and upon determination that the predetermined amount of insulin is needed, determining when to prompt the user to administer an additional dose of insulin comprising the predetermined amount of insulin, wherein the mobile communication device is implemented on a smartphone, a tablet, a wearable computing device including a smartwatch or smartglasses, or one or more computers networked in a communication network through the Internet, wherein determining when to prompt the user to administer the additional dose of insulin includes presenting a first alarm to the user upon a determination that a projected change in the blood sugar level caused by administration of the predetermined amount of insulin is greater than or equal to a particular value over the predetermined blood sugar level.

2. The method of claim 1, wherein the predetermined amount of insulin includes 1, 2, or 5 units of insulin.

3. The method of claim 1, wherein determining when to prompt the user to administer the additional dose of insulin includes presenting a second alarm to the user upon a determination that an amount of additional dose of insulin that needs to be administered exceeds one or more predetermined threshold values.

4. The method of claim 1, wherein the particular value is at least 20 mg/dL.

5. The method of claim 1, wherein the determining whether the predetermined amount of insulin is needed includes calculating an amount of insulin needed by:

$$\text{insulin needed} = ((\text{current blood sugar} - \text{target blood sugar})/\text{correction factor}) - \text{insulin on board}.$$

6. A diabetes management system for applying an algorithm, comprising:

an insulin delivery pen, including a dose setting and dispensing mechanism to set and dispense a dose of insulin, a sensor to detect an occurrence of a dispensing event of the insulin by the insulin delivery pen, and electronic circuits including a processor, a memory comprising instructions executable by the processor, and a wireless transmitter, the processor of the insulin delivery pen configured to generate dose data associated with the dispensing event of the dose of the insulin from the insulin delivery pen, and to wirelessly transmit the dose data; and a mobile communication device in wireless communication with the insulin delivery pen, the mobile communication device including a data processing unit including a processor and memory to receive and process the dose data, wherein the mobile communication device includes a software application program product comprising a non-transitory computer-readable storage medium having instructions, which when executed by the processor of the data processing unit, cause the mobile communication device to receive or determine a blood sugar level of a patient; receive or determine a dose amount of insulin delivered; based on the received or determined blood sugar level and the received or determined dose amount of insulin delivered, determine at the data processing unit whether a predetermined amount of insulin is needed to lower the blood sugar level to a predetermined blood sugar level; and upon determination that the predetermined amount of insulin is needed, determine at the data processing unit when to prompt a user of the system to administer an additional dose of insulin comprising the predetermined amount of insulin, wherein determining when to prompt the user to administer the additional dose of insulin includes presenting a first alarm to the user upon a determination that a projected change in the blood sugar level caused by administration of the predetermined amount of insulin is greater than or equal to a particular value over the predetermined blood sugar level.

7. The system of claim 6, wherein the dose amount of insulin delivered is determined based at mast in part on data received from the sensor detecting the dispensing event of the insulin by the insulin delivery pen.

8. The system of claim 6, wherein the predetermined amount of insulin includes 1, 2, or 5 units of insulin.

9. The system of claim 6, wherein determining when to prompt the user to administer the additional dose of insulin includes presenting a second alarm to the user upon a determination that an amount of additional dose of insulin that needs to be administered exceeds one or more predetermined threshold values.

10. The system of claim 9, wherein the second alarm is presented via one or more of an audio display, a visual display or a haptic display on one or both of the insulin delivery pen and the mobile communication device.

11. The system of claim 6, wherein the particular value is at least 20 mg/dL.

12. The system of claim 6, wherein the first alarm is presented via one or more of an audio display, a visual display or a haptic display on one or both of the insulin delivery pen and the mobile communication device.

13. The system of claim 6, wherein the mobile communication device is implemented on one or more of a smartphone, a tablet, a wearable computing device including a smartwatch or smartglasses, a computer including a laptop computer, or one or more computers networked in a communication network through the Internet.

14. The system of claim 6, wherein determining whether the predetermined amount of insulin is needed includes calculating an amount of insulin needed by:

$$\text{insulin needed} = ((\text{current blood sugar} - \text{target blood sugar})/\text{correction factor}) - \text{insulin on board}.$$

15. A diabetes management system, comprising:

an insulin delivery pen, including a dose setting and dispensing mechanism to set and dispense a dose of insulin, a sensor to detect an occurrence of a dispensing event of the insulin by the insulin delivery pen, and electronic circuits including a processor, a memory comprising instructions executable by the processor, and a wireless transmitter, the processor of the insulin delivery pen configured to generate dose data associated with the dispensing event of the dose of the insulin from the insulin delivery pen, and to wirelessly transmit the dose data; and a mobile communication device in wireless communication with the insulin delivery pen, the mobile communication device including a data processing unit including a processor and memory to receive and process the dose data, wherein the mobile communication device includes a software application program product comprising a non-transitory computer-readable storage medium having instructions executable by the processor of the data processing unit, wherein the data processing unit of the mobile communication device includes a dose calculator module that calculates a recommended dose of the insulin, and wherein the dose calculator module is in a disabled state at default, wherein, when instructions of the software application product are executed by the processor of the data processing unit, cause the mobile communication device to detect the insulin delivery pen is available for pairing; pair with the detected insulin delivery pen; and enable the dose calculator module on the mobile communication device after the pairing is successful.

16. The system of claim 15, wherein the mobile communication device is configured to receive a user touch input indicating an activation of one or more preexisting timed settings for delivering a dose of medication.

17. The system of claim 16, wherein the one or more preexisting timed settings include a single timed setting or four timed settings including a breakfast meal, a lunch meal, a dinner meal, and a snack.

18. The system of claim 15, wherein the mobile communication device is implemented on one or more of a smartphone, a tablet, a wearable computing device including a smartwatch or smartglasses, a computer including a laptop computer, or one or more computers networked in a communication network through the Internet.

* * * * *